United States Patent [19]

Narukawa et al.

[11] Patent Number: 4,833,181

[45] Date of Patent: May 23, 1989

[54] POLYOLEFIN COMPOSITION CONTAINING CELLULOSE FIBERS AND A DEODORIZER

[75] Inventors: Kiyotada Narukawa, Tokorozawa; Masakichi Shimada, Wakoh; Noboru Yamamoto, Tokyo; Taizo Yamaguchi, Tamagawa; Hiroyuki Wakabayashi; Fumio Kato, both of Kariya; Tamotsu Matsubara, Chiryu, all of Japan

[73] Assignees: Tonen Sekiyukagaku Kabushiki Kaisha, Tokyo; Nippondenso Co., Ltd., Kariya, both of Japan

[21] Appl. No.: 75,911

[22] Filed: Jul. 20, 1987

[30] Foreign Application Priority Data

Jul. 25, 1986 [JP] Japan ............................. 61-175210
Jul. 25, 1986 [JP] Japan ............................. 61-175213
Jul. 25, 1986 [JP] Japan ............................. 61-175214
Jul. 25, 1986 [JP] Japan ............................. 61-175215

[51] Int. Cl.$^4$ ................. C08L 89/00; C08L 23/04; D04H 1/42
[52] U.S. Cl. ............................ 524/13; 524/35; 524/115; 524/394; 524/424; 524/432; 524/433
[58] Field of Search .............. 524/13, 14, 38, 115, 524/301, 394, 424, 432, 433

[56] References Cited

U.S. PATENT DOCUMENTS 4,340,513 7/1982 Moteki et al. ..................... 524/13
4,409,345 10/1983 Moteki et al. ..................... 524/13

FOREIGN PATENT DOCUMENTS 52-36134 6/1977 Japan .
56-9576 2/1981 Japan .

Primary Examiner—John Kight
Assistant Examiner—Nathan M. Nutter
Attorney, Agent, or Firm—Armstrong, Nikaido, Marmelstein, Kubovcik & Murray

[57] ABSTRACT

A polyolefin composition comprising (a) polyolefin, (b) vegetable fibers mainly composed of cellulose fibers, and (c) a deodorizer selected from the group consisting of a combination of a metallic soap and an amine antioxidant, activated carbon, zeolite and a phosphorus compound. Because of the deodorizer, the polyolefin composition has substantially no odor without sacrificing mechanical properties thereof. Accordingly, it may be used suitably for car parts required to have high mechanical strength with substantially no odor, such as unit cases of air conditioners.

18 Claims, No Drawings

POLYOLEFIN COMPOSITION CONTAINING CELLULOSE FIBERS AND A DEODORIZER

BACKGROUND OF THE INVENTION

The present invention relates to a polyolefin composition with extremely little odor containing vegetable fibers mainly composed of cellulose fibers.

Since polyolefins such as polypropylene have excellent mechanical properties and moldability, they are widely used for injection molding, extrusion molding, etc.

In order to improve the mechanical strength of such polyolefins, various fillers and additives are added thereto. Particularly to improve the mechanical strength, workability and dimension stability thereof, the addition of cellulose fillers such as pulverized wood chips, pulps, sawdust, rice hulls and used papers was proposed. For instance, Japanese Patent Laid-Open No. 60-158236 discloses polyolefin resin composition comprising a polyolefin resin containing chemically modified polyolefin and vegetable fibers mainly composed of cellulose fibers.

Among the above cellulose fillers, used papers and paper scraps are particularly advantageous as fillers for polyolefin compositions because of their low costs.

It has been found, however, that the incorporation of such cellulose fillers into polyolefins provide the resulting moldings with intolerable odor. The reasons therefor are not necessarily clear, but it may be considered that because of heat generated when polyolefins and fillers are blended and molded, the used papers or paper scraps are decomposed to generate aldehydes, alcohols, organic acids, ketones, etc. It is known as a deodorizing method to evacuate a molding machine through vent holes while molding polyolefin compositions to withdraw smelling materials to the outside, or to add a small amount of water simultaneously with charging the polyolefin compositions into the molding machine to withdraw the smelling materials to the outside together with steam. These methods, however, fail to provide molded products of acceptable odor level.

OBJECT AND SUMMARY OF THE INVENTION

An object of the present invention is, therefore, to provide a polyolefin composition having excellent mechanical properties and moldability with substantially no odor, containing vegetable fibers mainly composed of cellulose fibers.

As a result of intense research in view of this object, the inventors have found that polyolefin moldings with extremely little odor can be obtained by incorporating into a polyolefin composition a deodorizer selected from the group consisting of a combination of a metallic soap and an amine antioxidant, activated carbon, zeolite and a phosphorus compound. The present invention is based on this finding.

That is, the polyolefin composition according to the present invention is characterized by comprising (a) polyolefin, (b) vegetable fibers mainly composed of cellulose fibers, and (c) a deodorizer selected from the group consisting of a combination of a metallic soap and an amine antioxidant, activated carbon, zeolite and a phosphorus compound.

DETAILED DESCRIPTION OF THE INVENTION

Polyolefins which may be used in the present invention include homopolymers of $\alpha$-olefins such as ethylene, propylene, butene-1, pentene-1, hexene-1, methylpentene-1, etc., copolymers of ethylene or propylene and other $\alpha$-olefins and copolymers of two or more of these $\alpha$-olefins. Among the above polyolefins, polymers based on propylene such as polypropylene and random or block copolymers of propylene and ethylene or other $\alpha$-olefins are preferable. The polyolefins may contain elastomers such as ethylene-propylene rubber and ethylene-propylene-diene copolymer.

Since the polyolefins themselves are non-polar resins, they may be mixed with adhesive polyolefin resins to increase the adhesion with vegetable fibers mainly composed of hydrophilic cellulose, thereby providing high-strength compositions. The adhesive polyolefin resins usable for this purpose include (a) modified polyolefins prepared by adding unsaturated carboxylic acids or their derivatives to polyolefins, (b) copolymers of olefins and unsaturated acids or their derivatives, and (c) copolymers of olefins and vinyl esters.

Polyolefins forming the backbones of the above modified polyolefins may be those described above. Unsaturated carboxylic acids or their derivatives which may be used for modifying polyolefins include acrylic acid, methacrylic acid, maleic acid, fumaric acid, citraconic acid, itaconic acid, endo-bicyclo(2,2,1)-5-heptene-2,3-dicarboxylic acid, endo-bicyclo(2,2,1)-1,4,5,6,7,7-hexachloro-5-heptene-2,3-dicarboxylic acid, cis-4-cyclohexene-1,2-dicarboxylic acid, etc. The derivatives of unsaturated carboxylic acids include anhydrides and esters, such as maleic anhydride, citraconic anhydride, endo-bicyclo(2,2,1)-1,4,5,6,7,7-hexachloro-5-heptene-2,3-dicarboxylic anhydride, endo-bicyclo(2,2,1)-5-heptene-2,3-dicarboxylic anhydride, cis-4-cyclohexene-1,2-dicarboxylic anhydride, methyl acrylate, methyl methacrylate, ethyl acrylate, ethyl methacrylate, butyl acrylate, butyl methacrylate, maleate (monoester, diester), etc. The amount of unsaturated carboxylic acid or its derivative in the modified polyolefin is 0.02–2 weight % based on the polyolefin backbone, preferably 0.05–1 weight %.

The addition reaction of unsaturated carboxylic acid or its derivative to polyolefin can be carried out by various known methods. For instance, it may be carried out by mixing polyolefin with unsaturated carboxylic acid or its derivative together with a reaction initiator such as an organic peroxide and then kneading the resulting mixture in a molten state.

Various olefins may be copolymerized with unsaturated acids or their derivatives or vinyl esters, but ethylene or propylene is preferable. Unsaturated acids copolymerized with ethylene or propylene are preferably the above-described acrylic acids, and their derivatives are preferably anhydrides thereof. And the vinyl esters may be those represented by the general formula: $CH_2=CHOCOR$ wherein R is an alkyl group, etc. Preferred Examples thereof are vinyl acetate, vinyl propionate, vinyl butyrate, etc., and particularly vinyl acetate is most preferable. Accordingly, the preferred copolymers are ethylene-acrylic acid copolymer, ethylene-methyl acrylate copolymer, ethylene-butyl acrylate copolymer, ethylene-vinyl acetate copolymer, etc.

The above copolymers may be random copolymers or block copolymers. The content of unsaturated acid or its derivative or vinyl ester in the copolymer is 1–50 weight % based on the copolymer, and preferably 3–40 weight %.

In view of the above, it should be understood that the term "polyolefins" used herein generally means polymers based on olefins, including olefin homopolymers, copolymers of two or more olefins which may contain olefin elastomers and adhesive polyolefin resins. The adhesive polyolefin resin is preferably 3–90 weight % based on the total polyolefin and more preferably 10–30 weight %.

The vegetable fibers mainly composed of cellulose fibers used in the present invention may be those fibrillated by sufficiently beating used papers or paper scraps. To obtain polyolefin compositions with improved mechanical strength and moldability, the vegetable fibers based on cellulose should be 10–60 weight % based on the total of the polyolefin and the vegetable fibers. When the vegetable fibers are less than 10 weight %, sufficient effects of increasing strength, hardness and heat resistance by cellulose fibers cannot be obtained. And when they exceed 60 weight %, the resulting compositions become brittle and poor in fluidity, rendering the compositions useless in practical applications. The preferred amount of the vegetable fibers is 15–50 weight %.

The deodorizer used in the present invention may be a combination of a metallic soap and an amine antioxidant, activated carbon, zeolite or a phosphorus compound.

The metallic soap is made of a metal in the Group IIa or IIb of the Periodic Table or aluminum and an organic carboxylic acid having 10–32 carbon atoms. The preferred metal component is magnesium, calcium, strontium, barium, zinc, cadmium or aluminum. Specific examples of the metallic soap are calcium stearate, calcium palmitate, calcium laurate, magnesium stearate, barium stearate, aluminum stearate, zinc stearate, zinc laurate, etc. Among them, calcium stearate is preferable.

The amount of the metallic soap added to the polyolefin composition is preferably 0.05–5 parts by weight per 100 parts by weight of the polyolefin-vegetable fiber mixture. When it is less than 0.05 parts by weight, deodorizing effects cannot be obtained, and when it exceeds 5 parts by weight, the resulting moldings have undesirably low mechanical properties.

The amine antioxidant added in combination with the above metallic soap in the present invention may be poly(2,2,4-trimethyl-1,2-dihydroquinoline), phenyl-α-naphthylamine, alkylated derivatives of phenyl-α-naphthylamine, octylated diphenylamine, alkylated diphenylamine, 4,4′-(α,α-dimethylbenzyl)diphenylamine, N,N′-dinaphthyl-p-phenylenediamine, N,N′-diphenyl-p-phenylenediamine, N-phenyl-N′-isopropyl-p-phenylenediamine, etc. Among them, poly(2,2,4-trimethyl-1,2-dihydroquinoline), 4,4′-(α,α-dimethylbenzyl)diphenylamine, and phenyl-α-naphthylamine are preferable. The amount of the amine antioxidant is preferably 0.05–5 parts by weight per 100 parts by weight of the polyolefin-vegetable fiber mixture. When it is less than 0.05 parts by weight, deodorizing effects cannot be obtained, and when it exceeds 5 parts by weight, the odor of the amine antioxidant itself comes out, leading to undesirable results. The more preferred amount of the amine antioxidant is 0.1–1.0 parts by weight.

The activated carbon used as a deodorizer in the present invention may be crushed carbon, granulated carbon, fibrous carbon, etc., but the crushed carbon and the granulated carbon are preferable from the economic point of view.

The pore radius of the activated carbon is preferably 6 Å or more. When it is less than 6 Å, it does not have sufficient ability to adsorb odor-generating components. The preferred pore radius is 10 Å or more. And with respect to a specific surface area of the activated carbon, it is preferably 700 m$^2$/g or more. When it is less than 700 m$^2$/g, a large amount of the activated carbon should be added, resulting in low efficiency and the decrease in mechanical properties of the resulting composition.

The amount of the activated carbon is 0.05–5 parts by weight per 100 parts by weight of the total of the polyolefin and the vegetable fibers. When it is less than 0.05 parts by weight, sufficient deodorizing effects cannot be obtained, and when it exceeds 5 parts by weight, the resulting composition moldings do not have high mechanical properties. The preferred amount of the activated carbon is 1–3 parts by weight.

Zeolite used as a deodorizer in the present invention is an aluminosilicate of an alkali metal or an alkali earth metal having a three-dimensional structure. Natural zeolite and glauconite may be used as natural products, but synthetic zeolite may also be used. Specific examples of the synthetic zeolite are zeolite A ($Na_2O.Al_2O_3.1.4$–$2.4SiO_2.5$–$6H_2O$), zeolite X ($0.7$–$1.1Na_2O.Al_2O_3.2$–$3SiO_2$.nearly $6H_2O$), zeolite Y ($0.7$–$1.1Na_2O.Al_2O_3.3$–$6SiO_2$.nearly $9H_2O$), zeolite L ($K_2. Na_2$)$O.Al_2O_3.5.2$–$7.0SiO_2$.nearly $5H_2O(K \geq Na)$, mordenite ($Na_2O.Al_2O_3.8.3$–$10SiO_2$.nearly $6H_2O$), etc.

The zeolite preferably has an average pore radius of 1 Å or more. When the pore radius is less than 1 Å, it does not have sufficient ability to adsorb components generating odor.

And the zeolite has preferably 700 m$^2$/g or more of a specific surface area. When it is less than 700 m$^2$/g, a large amount of the zeolite should be added, resulting in low efficiency and the decrease in mechanical properties of the resulting moldings.

The amount of the zeolite is 0.05–5 parts by weight per 100 parts by weight of the total of the polyolefin and the vegetable fibers. When it is less than 0.05 parts by weight, sufficient deodorizing effects cannot be obtained, and when it exceeds 5 parts by weight, the resulting composition moldings have low mechanical properties. The preferred amount of the zeolite is 1–3 parts by weight.

The phosphorus compound used as a deodorizer in the present invention is generally what is used as a phosphorus flame retardant, such as high-molecular phosphorus-nitrogen compounds and phosphorus esters. The high-molecular phosphorus-nitrogen compounds include condensed phosphoric acid carbamate, carbamyl polyphosphoric acid ammonium, etc. And the phosphoric acid esters include non-halogenous phosphoric acid esters such as trimethyl phosphate, triethyl phosphate, tributyl phosphate, trioctyl phosphate, tributoxyethyl phosphate, triphenyl phosphate, tricresyl phosphate, cresyldiphenyl phosphate, octyldiphenyl phosphate, bis(1,3-phenylene-diphenyl)phosphate, etc.; halogen-containing esters such as tris(chloroethyl)phosphate, tris(dichloropropyl)phosphate, tris(chloropropyl)phosphate, bis(2,3-dibromopropyl)-2,3-dichloropropyl phosphate, tris(2,3-dibromopropyl)phosphate, bis(chloropropyl)monooctyl phosphate, etc.: and special phosphoric acid esters such as polyphosphate ("Phosguard C-22-R" and "Phosguard 2-XC-20" manufactured by Monsanto Chemical, and "CR-505" manufactured by Daihachi Kagaku) and aromatic polyphosphate ("CR-720" manufactured by Daihachi Kagaku).

The amount of the phosphorus compound is 0.5–20 parts by weight per 100 parts by weight of the total of the polyolefin and the vegetable fibers. When the phosphorus compound is less than 0.5 parts by weight, substantially no deodorizing effects are obtained, and when it exceeds 20 parts by weight, the resulting moldings have low mechanical properties. The preferred amount of the phosphorus compound is 1-15 parts by weight.

In order to further increase the effects of the addition of the deodorizer in the present invention, it is preferable to add an antioxidant. The antioxidants which may be added to the polyolefin composition of the present invention include hindered phenol antioxidants, thioester antioxidants and reactive amine compounds.

The hindered phenol antioxidants include 2,6-di-t-butyl-4-methylphenol, 1,1,3-tris(2-methyl-4-hydroxy-5-t-butylphenyl)butane, tetrakis(methylene-3-(3,5-di-t-butyl-4-hydroxyphenyl)propionate/methane, n-octadecyl-β-(4'-hydroxy-3',5'-di-t-butylphenyl)propionate, 1,3,5-trimethyl-2,4,6-tris(3,5-di-t-butyl-4-hydroxybenzyl)benzene, tris(3,5-di-t-butyl-4-hydroxybenzyl)isocyanurate, etc.

The thioester antioxidants include dilauryl-thio-dipropionate, distearyl-thio-dipropionate, laurylstearyl-thio-dipropionate, dimyristyl-thio-dipropionate, tetrakis(methylene-3-dodecyl-thio-propionate)methane, 4,4'-thio-bis(3-methyl-6-t-butylphenol), 4,4'-thio-bis(2-methyl-6-butylphenol), 2,2'-thio-bis(4-methyl-6-t-butylphenol), etc.

The reactive amine compounds include monoethanol amine, diethanol amine, triethanol amine, ethylene diamine, hexamethylene diamine, etc. They are added particularly when a combination of the metallic soap and the amine antioxidant is used.

The amount of the above antioxidant is 0.05–5.0 parts by weight per 100 parts by weight of the polyolefin-vegetable fiber mixture, and preferably 0.1–2.0 parts by weight.

In order to further improve the appearance of the moldings prepared from the polyolefin composition of the present invention, various pigments and inorganic fillers, retardants, etc. may be added.

The polyolefin composition of the present invention may be prepared by kneading in a molten state by a kneader such as a single-screw extruder, a double-screw extruder, Banbury mixer and Brabender or a mixer such as a Henschel mixer. To make sure that the advantageous-natures of the cellulose fibers are fully utilized, it is desirable to use a kneading method capable of providing good dispersion of the fibers without breaking and carbonizing the fibers.

The present invention will be explained in further detail by the following Examples.

Incidentally, in each Example, tests were carried out by the following methods.

Odor: Testing the odors generated from molten compositions during the molding process and the odors generated from the resulting moldings, and indicating the odors by the following three levels.
Excellent: Substantially no odor
Good: Slight odor
Poor: Extreme odor
Tensile strength: measured by JIS K7113-71
Flexural modulus: measured by JIS K7203-73
Izot impact strength: measured by JIS K7110

EXAMPLES 1–15

100 parts by weight of a mixture consisting of 56 weight % of propylene-ethylene random copolymer (ethylene content 2%, MFR30) as a polyolefin component, 14 weight % of maleic anhydride-modified propylene-ethylene block copolymer (added acid 0.15 weight %) as a modified adhesive polyolefin resin and 30 weight % of finely divided newspapers were mixed with 0.1 parts by weight of tetrakis(methylene-3-(3,5-di-t-butyl-4-hydroxyphenyl-propionate)methane, and various types of metallic soap, amine antioxidants and reactive amine compounds shown in Table 1, and kneaded in a mixer while heating. The finely divided newspapers were broken into cellulose fibers during the kneading operation.

The kneaded mixture was cooled and pulverized to form granules, which were then charged into an injection molding machine to prepare specimens for testing their properties. Also, the resulting compositions were formed into heater cases for car air conditioners, and the odor was tested during the molding operation and on the molded products. The results are shown in Table 1.

COMPARATIVE EXAMPLES 1–4

Example 1 was repeated except for not adding one or both of the metallic soap and the amine antioxidant to prepare specimens for testing their properties. The test results are also shown in Table 1.

TABLE 1

| | Additive | | | | | | Odor Test | | Properties | | |
|---|---|---|---|---|---|---|---|---|---|---|---|
| | Metallic Soap | | Amine Antioxidant | | Amine Compound | | During | Molded | Tensile Strength | Flexural Modulus | Izot Impact Strength |
| No.(1) | Type | Wt. Parts | Type | Wt. Parts | Type | Wt. Parts | Molding | Product | (kg/cm$^2$) | (kg/cm$^2$) | (kg · cm/cm) |
| 1 | CaS | 0.1 | DMBDPA | 0.3 | — | — | good | good | 470 | 27,200 | 3.6 |
| 2 | " | 0.2 | " | 0.3 | — | — | good | good | 440 | 25,500 | 3.8 |
| 3 | " | 1.0 | " | 0.3 | — | — | good | good | 415 | 25,100 | 3.3 |
| 4 | " | 3.0 | " | 0.3 | — | — | good | good | 245 | 24,700 | 2.9 |
| 5 | " | 0.1 | " | 0.4 | — | — | excel. | excel. | 250 | 26,700 | 3.3 |
| 6 | " | 0.1 | " | 0.5 | — | — | excel. | excel. | 465 | 27,000 | 3.2 |
| 7 | Mgs | 0.1 | " | 0.3 | — | — | good | good | 450 | 26,200 | 3.5 |
| 8 | ZnS | 0.1 | " | 0.3 | — | — | good | good | 460 | 25,500 | 3.4 |
| 9 | AlS | 0.1 | " | 0.3 | — | — | good | good | 470 | 25,100 | 3.6 |
| 10 | CaL | 0.1 | " | 0.3 | — | — | good | good | 465 | 25,300 | 3.4 |
| 11 | ZnL | 0.1 | " | 0.3 | — | — | good | good | 460 | 27,000 | 3.2 |
| 12 | CaS | 0.1 | PNA | 0.4 | — | — | good | good | 450 | 27,100 | 3.4 |
| 13 | " | 0.1 | PIPPD | 0.4 | — | — | good | good | 450 | 26,800 | 3.5 |
| 14 | " | 0.1 | PTMDHQ | 0.4 | — | — | good | good | 450 | 26,900 | 3.4 |
| 15 | " | 0.1 | DMBDPA | 0.4 | DEA | 0.1 | excel. | excel. | 450 | 27,100 | 3.2 |

TABLE 1-continued

| | Additive | | | | | | Odor Test | | Properties | | |
|---|---|---|---|---|---|---|---|---|---|---|---|
| | Metallic Soap | | Amine Antioxidant | | Amine Compound | | During | Molded | Tensile Strength | Flexural Modulus | Izot Impact Strength |
| No.[1] | Type | Wt. Parts | Type | Wt. Parts | Type | Wt. Parts | Molding | Product | ($kg/cm^2$) | ($kg/cm^2$) | (kg · cm/cm) |
| 1' | — | — | — | — | — | — | poor | poor | 440 | 25,300 | 3.6 |
| 2' | CaS | 0.03 | — | — | — | — | poor | poor | 430 | 25,800 | 3.4 |
| 3' | — | — | DMBDPA | 0.5 | — | — | poor | poor | 415 | 26,100 | 3.6 |
| 4' | — | — | " | 6.0 | — | — | poor | poor | 380 | 23,700 | 3.6 |

Note:
[1]Nos. 1–15: Examples of the present invention, Nos. 1'–4': Comparative Examples
CaS: Calcium stearate
MgS: Magnesium stearate
ZnS: Zinc stearate
AlS: Aluminum stearate
CaL: Calcium laurate
ZnL: Zinc laurate
DEA: Diethanolamine
DMBDPA: 4,4'-(α,α-dimethylbenzyl)diphenylamine
PNA: Phenyl-α-naphthylamine
PIPPD: N—phenyl-N'—isopropyl-β-phenylenediamine
PTMDHQ: poly(2,2,4-trimethyl-1,2-dihydroquinoline)

EXAMPLES 16–25

As a polyolefin, propylene homopolymer (MFR20: H-PP), propylene-ethylene block copolymer (ethylene content 7.7%, MFR15: B-PP), high-density polyethylene (MI12; HDPE), low-density polyethylene (MI20; LDPE), linear low-density polyethylene (MI22: LLDPE) and ethylene-propylene copolymer rubber (Mooney viscosity $ML_{1+8}$(127° C.20: EPR); as a modified polyolefin, a maleic anhydride-modified propylene-ethylene block copolymer (acid content 0.15 weight %; CMP), and used papers finely divided in advance were mixed in the proportions as shown in Table 2. 100 parts by weight of the resulting mixture was mixed with 0.1 parts by weight of tetrakis(methylene-3-(3,5-di-t-butyl-4-hydroxyphenyl)propionate)methane as a phenolic antioxidant, 0.1 parts by weight of calcium stearate and 0.4 parts by weight of 4,4'-(α,α-dimethylbenzyl)diphenylamine to prepare specimens in the same manner as in Example 1. The properties of the specimens were measured. The results are shown in Table 2.

COMPARATIVE EXAMPLES 5–11

Specimens were prepared by adding only used papers and propylene-ethylene random copolymer (ethylene content 2%, MFR30; R-PP) to the same polyolefin as in Examples 16–25, and their properties were measured. The results are also shown in Table 2.

TABLE 2

| | Composition (wt. %) | | | | | | | | | Odor Test | | Properties | | |
|---|---|---|---|---|---|---|---|---|---|---|---|---|---|---|
| | | | | | | | | | | During Molding | Molded Product | Tensile Strength ($kg/cm^2$) | Flexural Modulus ($kg/cm^2$) | Izot Impact Strength (kg · cm/cm) |
| No.[1] | H-PP | B-PP | R-PP | HDPE | LDPE | LLDPE | EPR | CMP | Paper[2] | | | | | |
| 16 | 56 | — | — | — | — | — | — | 14 | 30 | excel. | excel. | 505 | 31,400 | 1.2 |
| 17 | — | 56 | — | — | — | — | — | 14 | 30 | excel. | excel. | 480 | 28,600 | 3.5 |
| 18 | — | — | — | 56 | — | — | — | 14 | 30 | excel. | excel. | 465 | 27,200 | 4.3 |
| 19 | — | — | — | — | 56 | — | — | 14 | 30 | excel. | excel. | 385 | 13,000 | 12.3 |
| 20 | — | — | — | — | — | 56 | — | 14 | 30 | excel. | excel. | 365 | 13,800 | 15.4 |
| 21 | 44.8 | — | — | — | — | — | 11.2 | 14 | 30 | excel. | excel. | 420 | 18,400 | 10.4 |
| 22 | — | 66.5 | — | — | — | — | — | 3.5 | 30 | excel. | excel. | 455 | 28,000 | 3.5 |
| 23 | — | 76 | — | — | — | — | — | 14 | 10 | excel. | excel. | 370 | 18,200 | 5.5 |
| 24 | — | 46 | — | — | — | — | — | 14 | 40 | excel. | excel. | 455 | 32,900 | 3.4 |
| 25 | — | 36 | — | — | — | — | — | 14 | 50 | excel. | excel. | 445 | 38,400 | 3.5 |
| 5' | 70 | — | — | — | — | — | — | — | 30 | poor | poor | 390 | 28,300 | 1.1 |
| 6' | — | 70 | — | — | — | — | — | — | 30 | poor | poor | 300 | 27,800 | 2.8 |
| 7' | — | — | 70 | — | — | — | — | — | 30 | poor | poor | 265 | 21,400 | 1.6 |
| 8' | — | — | — | 70 | — | — | — | — | 30 | poor | poor | 360 | 20,000 | 7.2 |
| 9' | — | — | — | — | 70 | — | — | — | 30 | poor | poor | 140 | 13,000 | 8.3 |
| 10' | — | — | — | — | — | 70 | — | — | 30 | poor | poor | 130 | 13,800 | 9.2 |
| 11' | 56 | — | — | — | — | — | — | 14 | 30 | poor | poor | 285 | 17,900 | 9.8 |

Note:
[1]Nos. 16–25: Examples of the present invention, Nos. 5'–11': Comparative Examples
[2]Used newspapers

EXAMPLES 26–35

100 parts by weight of a mixture consisting of 56 weight % of propylene-ethylene random copolymer (ethylene content 2%, MFR30) as a polyolefin component, 14 weight % of maleic anhydride-modified propylene-ethylene block copolymer (added acid 0.15 weight %) as a modified adhesive polyolefin resin and 30 weight % of finely divided newspapers were mixed with 0.1 parts by weight of tetrakis(methylene-3-(3,5-di-t-butyl-4-hydroxyphenyl-propionate)methane, and activated carbon shown in Table 3, and kneaded in a mixer while heating. The finely divided newspapers were broken into cellulose fibers during the kneading operation.

The kneaded mixture was cooled and pulverized to form granules, which were then charged into an injection molding machine to prepare specimens for testing their properties. Also, the resulting compositions were formed into heater cases for car air conditioners, and the odor was tested during the molding operation and on the molded products. The results are shown in Table 3.

COMPARATIVE EXAMPLES 12-13

Example 26 was repeated except for not adding the activated carbon to prepare specimens for testing their properties. The test results are also shown in Table 3.

ethylene (MI22; LLDPE) and ethylene-propylene copolymer rubber (Mooney viscosity $ML_{1+8}(127°\,C.)20$; EPR); as a modified polyolefin, a maleic anhydride-modified propylene-ethylene block copolymer (acid content 0.15 weight %; CMP), and used papers finely divided in advance were mixed in the proportions as shown in Table 4. 100 parts by weight of the resulting mixture was mixed with 0.1 parts by weight of tetrakis(-methylene-3-(3,5-di-t-butyl-4-hydroxyphenyl)propionate)methane as a phenolic antioxidant, and 3 parts by weight of activated carbon having an average pore radius of 11-13 Å and a specific surface area of 1000 $m^2/g$ or more to prepare specimens in the same manner

TABLE 3

| | Activated Carbon | | | Odor Test | | Properties | | |
|---|---|---|---|---|---|---|---|---|
| No.(1) | Pore Radius Å | Specific Surface Area (m²/g) | Wt. Parts | During Molding | Molded Product | Tensile Strength (kg/cm²) | Flexural Modulus (kg/cm²) | Izot Impact Strength (kg · cm/cm) |
| 26 | 11-13 | 1,000< | 5 | excel. | excel. | 400 | 24,200 | 3.0 |
| 27 | 20-22 | 1,300< | 0.05 | good | good | 450 | 26,800 | 3.2 |
| 28 | 14-16 | 1,200< | 2 | excel. | excel. | 400 | 24,000 | 3.0 |
|  | 16-18 | 1,200< | 2 |  |  |  |  |  |
| 29 | 14-16 | 1,200< | 3 | excel. | excel. | 410 | 24,000 | 3.0 |
| 30 | 14-16 | 1,200< | 1 | excel. | excel. | 440 | 26,800 | 3.2 |
|  | 16-18 | 1,200< | 1 |  |  |  |  |  |
| 31 | 10-12 | 1,100< | 1 | excel. | excel. | 425 | 26,900 | 3.1 |
|  | 20-22 | 1,300< | 1 |  |  |  |  |  |
| 32 | 20-22 | 1,300< | 2 | excel. | excel. | 440 | 26,800 | 3.3 |
| 33 | 10-12 | 1,100< | 0.5 | excel. | excel. | 445 | 26,900 | 3.3 |
|  | 20-22 | 1,300< | 0.5 |  |  |  |  |  |
| 34 | 20-22 | 1,300< | 1 | excel. | excel. | 450 | 27,000 | 3.2 |
| 35 | 20-22 | 1,300< | 0.1 | good | good | 450 | 27,000 | 3.2 |
| 12' | 11-13 | 1,000< | 10 | excel. | excel. | 320 | 26,000 | 2.0 |
| 13' | 16-18 | 1,200< | 0.03 | poor | poor | 450 | 27,000 | 3.6 |

Note:
(1)Nos. 26-35: Examples of the present invention, Nos. 12'-13': Comparative Examples

EXAMPLES 36-46

As a polyolefin, propylene homopolymer (MFR20: H-PP), propylene-ethylene block copolymer (ethylene content 7.7%, MFR15; B-PP), propylene-ethylene random copolymer (ethylene content 2%, MFR30: R-PP), high-density polyethylene (MI12; HDPE), low-density polyethylene (MI20: LDPE), linear low-density polyethylene as in Example 26. The properties of the specimens were measured. The results are shown in Table 4.

COMPARATIVE EXAMPLES 14-20

Specimens were prepared from the same polyolefins as in Examples 36-46 without adding the activated carbon, and their properties were measured. The results are also shown in Table 4.

TABLE 4

| | Composition (wt. %) | | | | | | | | | Odor Test | | Properties | | |
|---|---|---|---|---|---|---|---|---|---|---|---|---|---|---|
| No.(1) | H-PP | B-PP | R-PP | HDPE | LDPE | LLDPE | EPR | CMP | Paper(2) | During Molding | Molded Product | Tensile Strength (kg/cm²) | Flexural Modulus (kg/cm²) | Izot Impact Strength (kg · cm/cm) |
| 36 | 56 | — | — | — | — | — | — | 14 | 30 | excel. | excel. | 490 | 31,600 | 1.3 |
| 37 | — | 56 | — | — | — | — | — | 14 | 30 | excel. | excel. | 475 | 28,700 | 3.4 |
| 38 | — | — | — | 56 | — | — | — | 14 | 30 | excel. | excel. | 465 | 27,300 | 4.4 |
| 39 | — | — | — | — | 56 | — | — | 14 | 30 | excel. | excel. | 380 | 13,100 | 13.1 |
| 40 | — | — | — | — | — | 56 | — | 14 | 30 | excel. | excel. | 360 | 13,500 | 15.0 |
| 41 | 44.8 | — | — | — | — | — | 11.2 | 14 | 30 | excel. | excel. | 425 | 18,100 | 10.4 |
| 42 | — | 66.5 | — | — | — | — | — | 3.5 | 30 | excel. | excel. | 450 | 28,300 | 3.3 |
| 43 | — | 76 | — | — | — | — | — | 14 | 10 | excel. | excel. | 360 | 18,200 | 5.8 |
| 44 | — | 46 | — | — | — | — | — | 14 | 40 | excel. | excel. | 445 | 32,500 | 3.0 |
| 45 | — | 36 | — | — | — | — | — | 14 | 50 | excel. | excel. | 455 | 38,800 | 3.7 |
| 46 | — | 49 | — | — | — | — | — | 21 | 30 | excel. | excel. | 490 | 29,000 | 2.8 |
| 14' | — | — | 70 | — | — | — | — | — | 30 | poor | poor | 270 | 21,400 | 1.6 |
| 15' | 70 | — | — | — | — | — | — | — | 30 | poor | poor | 395 | 28,000 | 1.3 |
| 16' | — | 70 | — | — | — | — | — | — | 30 | poor | poor | 290 | 27,200 | 2.6 |
| 17' | — | — | — | 70 | — | — | — | — | 30 | poor | poor | 365 | 19,800 | 7.5 |
| 18' | — | — | — | — | 70 | — | — | — | 30 | poor | poor | 135 | 13,200 | 8.4 |
| 19' | — | — | — | — | — | 70 | — | — | 30 | poor | poor | 130 | 13,800 | 9.8 |

TABLE 4-continued

| No.[1] | Composition (wt. %) | | | | | | | | | Odor Test | | Properties | | |
| | H-PP | B-PP | R-PP | HDPE | LDPE | LLDPE | EPR | CMP | Paper[2] | During Molding | Molded Product | Tensile Strength (kg/cm$^2$) | Flexural Modulus (kg/cm$^2$) | Izot Impact Strength (kg · cm/cm) |
|---|---|---|---|---|---|---|---|---|---|---|---|---|---|---|
| 20' | 56 | — | — | — | — | — | 14 | — | 30 | poor | poor | 290 | 17,500 | 10.0 |

Note:
[1]Nos. 36–46: Examples of the present invention, Nos. 14'–20': Comparative Examples
[2]Used newspapers

EXAMPLES 47–57

100 parts by weight of a mixture consisting of 56 weight % of propylene-ethylene random copolymer (ethylene content 2%, MFR30) as a polyolefin component, 14 weight % of maleic anhydride-modified propylene-ethylene block copolymer (added acid 0.15 weight %) as a modified polyolefin and 30 weight % of finely divided newspapers were mixed with 0.1 parts by weight of tetrakis(methylene-3-(3,5-di-t-butyl-4-hydroxyphenyl-propionate)methane, and various types of synthetic zeolite shown in Table 5, and kneaded in a mixer while heating. The finely divided newspapers were broken into cellulose fibers during the kneading operation.

The kneaded mixture was cooled and pulverized to form granules, which were then charged into an injection molding machine to prepare specimens for testing their properties. Also, the resulting compositions were formed into heater cases for car air conditioners, and the odor was tested during the molding operation and on the molded products. The results are shown in Table 5.

COMPARATIVE EXAMPLES 21–23

Example 1 was repeated except for adding zeolite in amounts outside the composition range of the present invention, to prepare specimens for testing their properties. The test results are also shown in Table 5.

EXAMPLES 58–68

As a polyolefin, propylene homopolymer (MFR20: H-PP), propylene-ethylene block copolymer (ethylene content 7.7%, MFR15; B-PP), propylene-ethylene random copolymer (ethylene content 2%, MFR30; R-PP), high-density polyethylene (MI12; HDPE), low-density polyethylene (MI20; LDPE), linear low-density polyethylene (MI22; LLDPE) and ethylene-propylene copolymer rubber (Mooney viscosity ML$_{1+8}$(127° C.)20; EPR); as a modified polyolefin, a maleic anhydride-modified propylene-ethylene block copolymer (acid content 0.15 weight %; CMP), and used papers finely divided in advance were mixed in the proportions as shown in Table 6. 100 parts by weight of the resulting mixture was mixed with 0.1 parts by weight of tetrakis(-methylene-3-(3,5-di-t-butyl-4-hydroxyphenyl)propionate)methane as a phenolic antioxidant, and 3 parts by weight of synthetic zeolite (average pore radius 2.5Å) to prepare specimens in the same manner as in Example 47. The properties of the specimens were measured. The results are shown in Table 6.

COMPARATIVE EXAMPLES 24–30

Specimens were prepared from the same polyolefins as in Examples 58–68 without adding the synthetic zeolite, and their properties were measured. The results are also shown in Table 6.

TABLE 5

| No.[1] | Synthetic Zeolite | | Odor Test | | Properties | | |
| | Average Pore Radius (Å) | Wt. Parts | During Molding | Molded Product | Tensile Strength (kg/cm$^2$) | Flexural Modulus (kg/cm$^2$) | Izot Impact Strength (kg · cm/cm) |
|---|---|---|---|---|---|---|---|
| 47 | 1.5 | 5 | excel. | excel. | 410 | 25,900 | 3.1 |
| 48 | 2 | 2 | excel. | excel. | 445 | 26,400 | 3.3 |
| 49 | 2.5 | 2 | excel. | excel. | 450 | 26,500 | 3.3 |
| 50 | 5 | 2 | excel. | excel. | 440 | 26,500 | 3.3 |
| 51 | 6.5 | 2 | excel. | excel. | 450 | 26,500 | 3.3 |
| 52 | 1.5 | 1 | excel. | excel. | 450 | 26,600 | 3.3 |
| 53 | 2 | 1 | excel. | excel. | 450 | 26,600 | 3.4 |
| 54 | 2.5 | 1 | excel. | excel. | 455 | 26,700 | 3.4 |
| 55 | 5 | 1 | excel. | excel. | 450 | 26,600 | 3.4 |
| 56 | 6.5 | 1 | excel. | excel. | 450 | 26,600 | 3.4 |
| 57 | 6.5 | 0.05 | good | good | 460 | 27,600 | 3.5 |
| 21' | 2 | 0.03 | poor | poor | 470 | 27,700 | 3.6 |
| 22' | 5 | 0.02 | poor | poor | 465 | 27,600 | 3.6 |
| 23' | 5 | 10 | excel. | excel. | 330 | 26,700 | 2.0 |

Note:
[1]Nos. 47–57: Examples of the present invention, Nos. 21'–23': Comparative Examples

TABLE 6

| No.[1] | Composition (wt. %) | | | | | | | | | Odor Test | | Tensile Strength (kg/cm$^2$) | Flexural Modulus (kg/cm$^2$) | Izot Impact Strength (kg · cm/cm) |
|---|---|---|---|---|---|---|---|---|---|---|---|---|---|---|
| | H-PP | B-PP | R-PP | HDPE | LDPE | LLDPE | EPR | CMP | Paper[2] | During Molding | Molded Product | | | |
| 58 | 56 | — | — | — | — | — | — | 14 | 30 | excel. | excel. | 500 | 32,100 | 1.1 |
| 59 | — | 56 | — | — | — | — | — | 14 | 30 | excel. | excel. | 480 | 29,900 | 3.1 |
| 60 | — | — | — | 56 | — | — | — | 14 | 30 | excel. | excel. | 465 | 27,500 | 4.7 |
| 61 | — | — | — | — | 56 | — | — | 14 | 30 | excel. | excel. | 395 | 12,900 | 14.0 |
| 62 | — | — | — | — | — | 56 | — | 14 | 30 | excel. | excel. | 370 | 13,800 | 14.5 |
| 63 | 44.8 | — | — | — | — | — | 11.2 | 14 | 30 | excel. | excel. | 440 | 17,700 | 10.5 |
| 64 | — | 66.5 | — | — | — | — | — | 3.5 | 30 | excel. | excel. | 445 | 28,300 | 3.4 |
| 65 | — | 76 | — | — | — | — | — | 14 | 10 | excel. | excel. | 375 | 19,100 | 5.1 |
| 66 | — | 46 | — | — | — | — | — | 14 | 40 | excel. | excel. | 460 | 33,000 | 2.9 |
| 67 | — | 36 | — | — | — | — | — | 14 | 50 | excel. | excel. | 470 | 33,400 | 3.1 |
| 68 | — | 49 | — | — | — | — | — | 21 | 30 | excel. | excel. | 490 | 28,900 | 3.7 |
| 24' | 70 | — | — | — | — | — | — | — | 30 | poor | poor | 395 | 28,000 | 1.3 |
| 25' | — | 70 | — | — | — | — | — | — | 30 | poor | poor | 290 | 27,200 | 2.6 |
| 26' | — | — | 70 | — | — | — | — | — | 30 | poor | poor | 280 | 22,800 | 1.9 |
| 27' | — | — | — | 70 | — | — | — | — | 30 | poor | poor | 365 | 19,800 | 7.5 |
| 28' | — | — | — | — | 70 | — | — | — | 30 | poor | poor | 135 | 13,200 | 8.4 |
| 29' | — | — | — | — | — | 70 | — | — | 30 | poor | poor | 130 | 13,800 | 9.8 |
| 30' | 56 | — | — | — | — | — | 14 | — | 30 | poor | poor | 290 | 17,500 | 10.0 |

Note:
[1]Nos. 58-68: Examples of the present invention, Nos. 24'-30': Comparative Examples
[2]Used newspapers

EXAMPLES 69-79

100 parts by weight of a mixture consisting of 56 weight % of propylene-ethylene random copolymer (ethylene content 2%, MFR30) as a polyolefin component, 14 weight % of maleic anhydride-modified propylene-ethylene block copolymer (added acid 0.15 weight %) as a modified adhesive polyolefin resin and 30 weight % of finely divided newspapers were mixed with 0.1 parts by weight of tetrakis(methylene-3-(3,5-di-t-butyl-4-hydroxyphenyl-propionate)methane, as a phenolic antioxidant, and a phosphorus compound as shown in Table 7, and kneaded in a mixer while heating. The finely divided newspapers were broken into cellulose fibers during the kneading operation.

The kneaded mixture was cooled and pulverized to form granules, which were then charged into an injection molding machine to prepare specimens for testing their properties. Also, the resulting compositions were formed into heater cases for car air conditioners, and the odor was tested during the molding operation and on the molded products. The results are shown in Table 7.

COMPARATIVE EXAMPLES 31-33

Example 69 was repeated except for adding the phosphorus compound in amounts outside the composition range of the present invention, to prepare specimens for testing their properties. The test results are also shown in Table 7.

TABLE 7

| No.[1] | Phosphorus Compound | | Odor Test | | Tensile Strength (kg/cm$^2$) | Flexural Modulus (kg/cm$^2$) | Izot Impact Strength (kg · cm/cm) |
|---|---|---|---|---|---|---|---|
| | Type | Wt. Parts | During Molding | Molded Product | | | |
| 69 | PNP | 0.5 | good | good | 450 | 26,500 | 3.1 |
| 70 | " | 1 | excel. | excel. | 455 | 26,800 | 2.9 |
| 71 | " | 5 | excel. | excel. | 430 | 28,100 | 2.2 |
| 72 | " | 10 | excel. | excel. | 405 | 30,400 | 1.8 |
| 73 | " | 15 | excel. | excel. | 380 | 33,500 | 1.5 |
| 74 | BPDPP | 1 | excel. | excel. | 435 | 26,700 | 2.5 |
| 75 | " | 5 | excel. | excel. | 435 | 28,000 | 2.3 |
| 76 | TPP | 5 | excel. | excel. | 430 | 27,500 | 2.4 |
| 77 | CDPP | 5 | excel. | excel. | 435 | 28,000 | 2.3 |
| 78 | TCEP | 5 | excel. | excel. | 425 | 29,000 | 2.2 |
| 79 | APP | 5 | excel. | excel. | 435 | 28,500 | 2.1 |
| 31' | — | — | poor | poor | 450 | 26,400 | 3.3 |
| 32' | PNP | 0.2 | poor | poor | 455 | 26,400 | 3.1 |
| 33' | BPDPP | 0.2 | poor | poor | 450 | 25,900 | 3.0 |

Note:
[1]Nos. 69-79: Examples of the present invention, Nos. 31'-33': Comparative Examples
PNP: High-Molecular phosphorous-nitrogen compound ("Nonnen W-3" manufactured by Marubishi Petrochemical Industries, Co., Ltd.)
BPDPP: Bis(1,3-phenylene-diphenyl)phosphate ("MARK PFR" manufactured by Adeka Argus Chemical Ltd.)
TPP: Triphenyl phosphate (manufactured by Daihachi Kagaku)
CDPP: Cresyldiphenyl phosphate (manufactured by Daihachi Kagaku)
TCEP: Tris(chloroethyl)phosphate (manufactured by Daihachi Kagaku)
APP: Aromatic polyphosphate ("CR-720" manufactured by Daihachi Kagaku)

EXAMPLES 80-88

As a polyolefin, propylene homopolymer (MFR20: H-PP), propylene-ethylene block copolymer (ethylene content 7.7%, MFR15; B-PP), high-density polyethylene (MI12: HDPE), low-density polyethylene (MI20: LDPE), linear low-density polyethylene (MI22: LLDPE) and ethylene-propylene copolymer rubber (Mooney viscosity $ML_{1+8}(127°\ C.)20$; EPR); as a modified polyolefin, a maleic anhydride-modified propylene-ethylene block copolymer (acid content 0.15 weight %; CMP), and ethylene-vinyl acetate copolymer (MI30: EVA), and used papers finely divided in advance were mixed in the proportions as shown in Table 8. 100 parts by weight of the resulting mixture was mixed with 0.1 parts by weight of tetrakis(methylene-3-(3,5-di-t-butyl-4-hydroxyphenyl)propionate)methane as a phenolic antioxidant, and 5 parts by weight of the high-molecular phosphorus-nitrogen compound ("Nonnen W-3" manufactured by Marubishi Petrochemical Industries Co., Ltd.), to prepare specimens in the same manner as in Example 69. The properties of the specimens were measured. The results are shown in Table 8.

TABLE 8

| | Composition (wt. %) | | | | | | | | Odor Test | | Properties | | |
|---|---|---|---|---|---|---|---|---|---|---|---|---|---|
| | | | | | | | | | During Molding | Molded Product | Tensile Strength (kg/cm$^2$) | Flexural Modulus (kg/cm$^2$) | Izot Impact Strength (kg·cm/cm) |
| No.[1] | H-PP | B-PP | HDPE | LDPE | LLDPE | EPR | CMP | EVA | Paper[2] | | | | |
| 80 | 56 | — | — | — | — | — | 14 | — | 30 | excel. | excel. | 480 | 33,000 | 1.3 |
| 81 | — | 56 | — | — | — | — | 14 | — | 30 | excel. | excel. | 460 | 30,100 | 3.1 |
| 82 | — | — | 56 | — | — | — | 14 | — | 30 | excel. | excel. | 445 | 28,600 | 4.5 |
| 83 | — | — | — | 56 | — | — | 14 | — | 30 | excel. | excel. | 370 | 13,700 | 13.1 |
| 84 | — | — | — | — | 56 | — | 14 | — | 30 | excel. | excel. | 300 | 14,500 | 14.6 |
| 85 | 44.8 | — | — | — | — | 11.2 | 14 | — | 30 | excel. | excel. | 400 | 19,400 | 11.0 |
| 86 | — | 65 | — | — | — | — | — | 5 | 30 | excel. | excel. | 420 | 28,900 | 3.9 |
| 87 | — | 85 | — | — | — | — | — | 5 | 10 | excel. | excel. | 360 | 19,500 | 5.1 |
| 88 | — | 40 | — | — | — | — | — | 10 | 50 | excel. | excel. | 445 | 40,000 | 3.3 |

Note:
[1]Nos. 80–88: Examples of the present invention
[2]Used newspapers

As described above, the polyolefin composition of the present invention contains vegetable fibers mainly composed of cellulose fibers well dispersed in the polyolefin via adhesive polyolefin resins. Because of good adhesion of the cellulose fibers with the polyolefin, the polyolefin composition has excellent mechanical properties. Accordingly, it may be suitably subjected to injection molding for providing thin, large-scale parts. Further, since the odor problem has been solved, it may be used for any parts which should not generate odor, such as unit cases of air conditioners for cars.

What is claimed is:

1. A polyolefin composition comprising
(a) a polyolefin,
(b) vegetable fibers mainly composed of cellulose fibers, and
(c) a deodorizer selected from the group consisting of activated carbon, zeolite, a phosphorus compound, and a mixture of a metallic soap and an amine antioxidant.

2. The polyolefin composition according to claim 1, wherein said vegetable fibers are 10–60 weight % of the total of said polyolefin and said vegetable fibers.

3. The polyolefin composition according to claim 1, wherein said polyolefin contains an adhesive polyolefin resin in an amount of 3–90 weight % based on the total weight of said polyolefin.

4. The polyolefin composition according to claim 3, wherein said adhesive polyolefin resin is 10–30 weight % based on the total weight of said polyolefin.

5. The polyolefin composition according to claim 2, wherein said polyolefin contains an adhesive polyolefin resin in an amount of 3–90 weight % based on the total weight of said polyolefin.

6. The polyolefin composition according to claim 5, wherein said adhesive polyolefin resin is 10–30 weight % based on the total weight of said polyolefin.

7. The polyolefin composition according to claim 3, wherein said adhesive polyolefin resin is at least one of (a) modified polyolefin prepared by adding unsaturated carboxylic acid or a derivative thereof to polyolefin, (b) copolymer of olefin and unsaturated acid or a derivative thereof, and (c) copolymer of olefin and vinyl ester.

8. The polyolefin composition according to claim 7, wherein said modified polyolefin contains 0.02–2 weight % of unsaturated carboxylic acid or a derivative thereof.

9. The polyolefin composition according to claim 7, wherein said copolymer of olefin and unsaturated acid or a derivative thereof contains 1–50 weight % of said unsaturated acid or a derivative thereof.

10. The polyolefin composition according to claim 7, wherein said copolymer of olefin and vinyl ester contains 1–50 weight % of said vinyl ester.

11. The polyolefin composition according to claim 1, wherein said deodorizer is a combination of said metallic soap and said amine antioxidant, said metallic soap and said amine antioxidant being respectively 0.05–5 parts by weight per 100 parts by weight of the total of said polyolefin and said vegetable fibers.

12. The polyolefin composition according to claim 11, wherein said metallic soap is a salt made of metal in the group IIa or IIb of the Periodic Table or aluminum and organic carboxylic acid having 10–32 carbon atoms.

13. The polyolefin composition according to claim 1, wherein said deodorizer is activated carbon in an amount of 0.05–5 parts by weight per 100 parts by weight of the total of said polyolefin and said vegetable fibers.

14. The polyolefin composition according to claim 13, wherein said activated carbon has an average pore radius of 6 Å or more and a specific surface area of 700 m$^2$/g or more.

15. The polyolefin composition according to claim 1, wherein said deodorizer is zeolite in an amount of 0.05–5 parts by weight per 100 parts by weight of the total of said polyolefin and said vegetable fibers.

16. The polyolefin composition according to claim 15, wherein said zeolite has an average pore radius of 1

Å or more and a specific surface area of 700 m²/g or more.

17. The polyolefin composition according to claim 1, wherein said deodorizer is a phosphorus compound in an amount of 0.5–20 parts by weight per 100 parts by weight of the total of said polyolefin and said vegetable fibers.

18. The polyolefin composition according to claim 17, wherein said phosphorus compound is a high-molecular phosphorus-nitrogen compound or a phosphorus ester.

* * * * *